United States Patent [19]

Hettche et al.

[11] Patent Number: 4,673,666

[45] Date of Patent: Jun. 16, 1987

[54] 2-AMINO-3-ETHOXYCARBONYLAMINO-6-(P-FLUORO-BENZYLAMINO)-PYRIDINE GLUCONATE AND PHARMACEUTICAL PREPARATIONS CONTAINING IT

[75] Inventors: Helmut Hettche, Offenbach; Peter Emig, Niederdorfelden; Jurgen Engel, Alzenau, all of Fed. Rep. of Germany

[73] Assignee: Degussa Aktiengesellschaft, Frankfurt am Main, Fed. Rep. of Germany

[21] Appl. No.: 729,413

[22] Filed: May 1, 1985

[30] Foreign Application Priority Data

May 5, 1984 [DE] Fed. Rep. of Germany ....... 3416609

[51] Int. Cl.$^4$ .......................... A61K 31/70; C07H 3/02
[52] U.S. Cl. ...................................... 514/23; 536/18.7
[58] Field of Search .......................... 536/18.7; 514/23

[56] References Cited

U.S. PATENT DOCUMENTS 4,481,205  11/1984  von Bebenburg et al. ......... 546/307

FOREIGN PATENT DOCUMENTS 1795858  1/1979  Fed. Rep. of Germany .
3133519  6/1982  Fed. Rep. of Germany .

Primary Examiner—Johnnie R. Brown
Assistant Examiner—Elli Peselev
Attorney, Agent, or Firm—Cushman, Darby & Cushman

[57]            ABSTRACT

There is disclosed 2-amino-3-ethoxycarbonylamino-6-(p-fluoro-benzylamino)-pyridine gluconate, process for its production and pharmaceutical preparations which contain this material.

18 Claims, 1 Drawing Figure

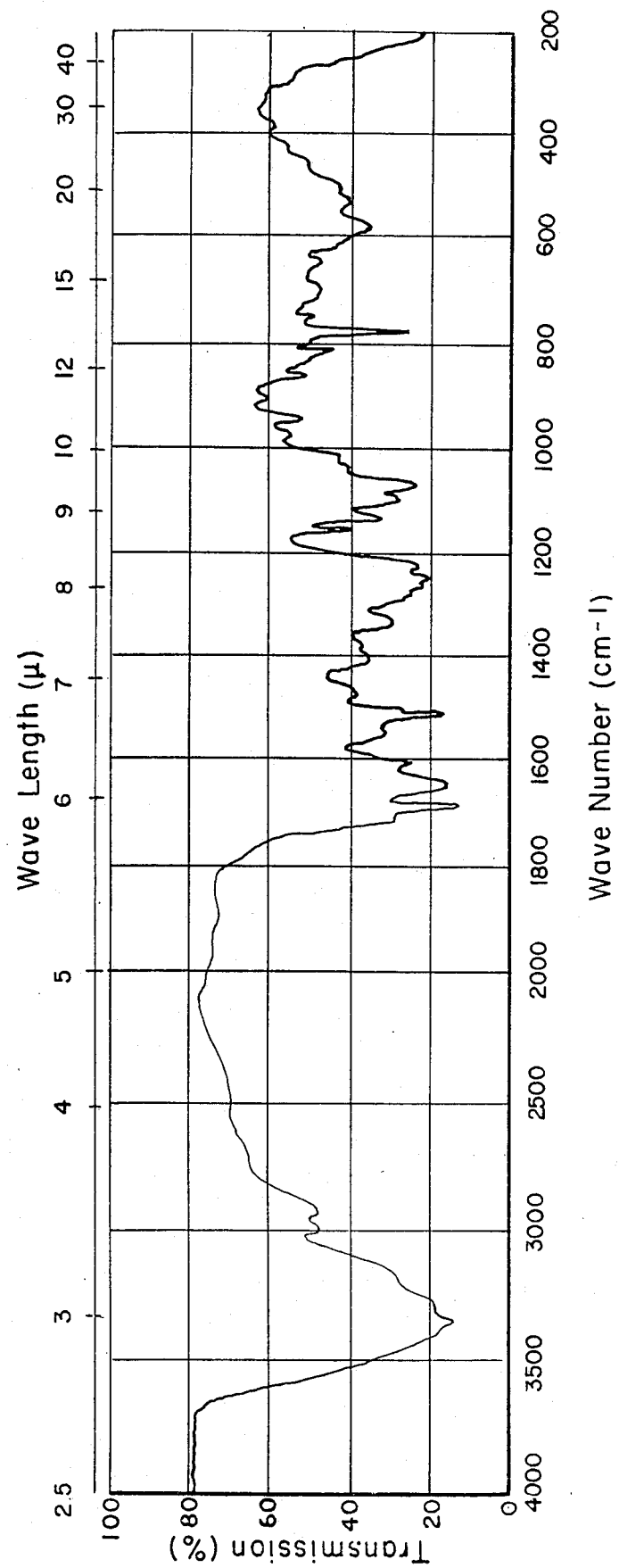

2-AMINO-3-ETHOXYCARBONYLAMINO-6-(P-FLUORO-BENZYLAMINO)-PYRIDINE GLUCONATE AND PHARMACEUTICAL PREPARATIONS CONTAINING IT

BACKGROUND OF THE INVENTION 2-amino-3-ethoxycarbonylamino-6-(p-fluoro-benzylamino)-pyridine hydrochloride is described in German Pat. No. 1795858. The compound is active as an antiphlogistic and an analgetic. 2-amino-3-ethoxycarbonylamino-6-(p-fluoro-benzylamino)-pyridine maleate described in German OS P 3133519.5 is suitable for the production of pharmaceutical preparations.

However, these salts are little suited to apply the active material in the form of a solution because of their slight solubility, poor stability in solution and insufficient venous compatibility.

Therefore it was the task of the invention to prepare additional suitable forms of preparation for 2-amino-3-ethoxycarbonylamino-6-(p-fluoro-benzylamino)-pyridine, for example injectable solutions.

SUMMARY OF THE INVENTION

There is prepared 2-amino-3-ethoxycarbonylamino-6-(p-fluoro-benzylamino)-pyridine gluconate having the chemical formula

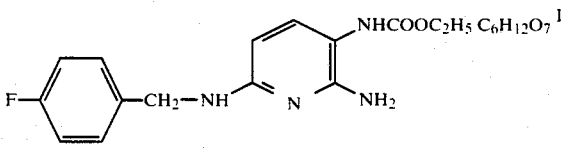

The 2-amino-3-ethoxycarbonylamino-6-(p-fluoro-benzylamino)-pyridine gluconate of formula I is made by a process of reacting 2-amino-3-ethoxycarbonylamino-6-(p-fluoro-benzylamino)-pyridine with gluconic acid with or without a solvent or with gluconic acid -$\Delta$-lactone in a solvent/water mixture at a temperature between 20° and 140° C.

There is provided a medicine which contains 2-amino-3-ethoxycarbonylamino-6-(p-fluoro-benzylamino)-pyridine gluconate as active material together with a customary pharmaceutical carrier and/or diluent.

The medicine can be in the form of an injectable solution. The injectable solution can have as solvent a mixture consisting of (or consisting essentially of) 10 to 95% polyethylene glycol and 5 to about 90% water or the solvent can consist of (or consist essentially of) a mixture of 10 to 95% glycofurol and 5 to about 90% water or the solvent can consist of (or consist essentially of) a mixture of 10 to 90% polyethylene glycol and 5 to 85% glycofurol and 5 to about 85% water.

The injectable solution of 2-amino-3-ethoxycarbonylamino-6-(p-fluoro-benzylamino)-pyridine gluconate can contain a pharmaceutically compatible organic acid. The injectable solution can contain excess free gluconic acid.

The medicine can be prepared by mixing 2-amino-3-ethoxycarbonylamino-6-(p-fluoro-benzylamino)-pyridine gluconate with customary pharmaceutical adjuvants and carriers or diluents.

A medicine containing 2-amino-3-ethoxycarbonylamino-6-(p-fluoro-benzylamino)-pyridine gluconate is prepared by mixing 2-amino-3-ethoxycarbonylamino-6-(p-fluoro-benzylamino)-pyridine or 2-amino-3-ethoxycarbonylamino-6-(p-fluoro-benzylamino)-pyridine gluconate together with excess gluconic acid-$\Delta$-lactone in a physiologically compatible solvent.

The invention also includes the use of gluconic acid or gluconic acid-$\Delta$-lactone to improve the solubility of 2-amino-3-ethoxycarbonylamino-6-(p-fluoro-benzylamino)-pyridine.

It has surprisingly been found that stable pharmaceutical preparations, especially solutions, can be produced from 2-amino-3-ethoxycarbonyl-amino-6-(p-fluoro-benzylamino)-pyridine gluconate. Besides it has been discovered that 2-amino-3-ethoxycarbonylamino-6-(p-fluoro-benzylamino)-pyridine gluconate in intravenous dosage has a better compatibility than the other known salts of 2-amino-3-ethoxycarbonylamino-6-(p-fluoro-benzylamino)-pyridine.

The 2-amino-3-ethoxycarbonylamino-6-(p-fluoro-benzylamino)-pyridine used for the production of the gluconate is described in German OS P 3133519.5.

The production of the 2-amino-3-ethoxycarbonylamino-6-(p-fluoro-benzylamino)-pyridine gluconate is carried out by reacting 2-amino-3-ethoxycarbonyl-amino-6-(p-fluoro-benzylamino)-pyridine with gluconic acid or gluconic acid-$\Delta$-lactone. This reaction can be carried out with or without solvent at a temperature between 20° C. and 140° C., preferably between 50° C. and 120° C.

As solvents there can be used for example lower alcohols (for example with 1–6 carbon atoms such as methanol, ethanol, n-propanol, isopropanol, n-butanol, 1,2-propanediol, 1,4-butanediol, n-pentanol, 3-pentanol, n-hexanol), lower ketones (for example with 1–6 carbon atoms such as acetone, 2-butanone, methyl isobutyl ketone, polyalkylene glycols (whereby alkylene indicates 2, 3, or 4 carbon atoms) having molecular weights between 190 and 7500 and cyclic saturated alcohols having 4 to 8, preferably 4 to 6 carbon atoms such as for example glycofurol as well as pharmaceutically usable organic acids and mixtures of these mediums with water.

In the event that there is employed gluconic acid-$\Delta$-lactone in place of gluconic acid there must be present a certain amount of water (for example 1 mole of water per 1 mole of lactone). For example it is advantageous to employ the gluconic acid-$\Delta$-lactone since it is available commercially in crystalline form and is quickly hydrolyzed in water to gluconic acid. For example the production can be carried out in the following manner.

1 mole of 2-amino-3-ethoxycarbonyl-amino-6-(p-fluoro-benzylamino)-pyridine was suspended in a given case, in a solvent (ethanol, 1,2-propanediol) and treated with a solution of 1 mole of gluconic acid-$\Delta$-lactone in an aqueous solvent (ethanol, 1,2-propanediol) prepared at a temperature between 20° C. and 140° C. or with 1 mole of gluconic acid with or without a solvent. The reaction mixture is allowed to react for some further time, preferably with heating (50° to 70° C.) and then in a given case, the solvent present evaporated. The residue remaining was resteamed and dried at elevated temperature in a vacuum. The salt was obtained in a yield of 90%, M.P.: 117° to 123° C.

The 2-amino-3-ethoxycarbonylamino-6-(p-fluoro-benzylamino)-pyridine gluconate is stable and shows no inclination to colorize during reaction with the free base or through oxidation, such as for example is observed with the hydrochloride.

Therefore the 2-amino-3-ethoxycarbonylamino-6-(p-fluoro-benzylamino)-pyridine gluconate is especially well suited for the production of pharmaceutical preparations. The 2-amino-3-ethoxycarbonylamino-6-(p-fluoro-benzylamino)-pyridine gluconate is very difficultly soluble in water, the solubility is increased by the addition of a physiologically compatible organic acid, for example lactic acid, glucuronic acid and/or gluconic acid. The solubility is especially increased considerably by the addition of excess gluconic acid.

There are suitable as solvents for the production of stable, injectable solutions of 2-amino-3-ethoxycarbonylamino-6-(p-fluoro-benzylamino)-pyridine gluconate physiologically compatible medicines for example polyethylene glycol-water mixtures or glycofurol-water mixtures in a given case with additional customary stabilizers and adjuvants. Preferably such solutions contain excess free gluconic acid.

For example, there is chosen an at least 1-fold, especially 1–6 fold, preferably 2 to 4 fold, molar excess (based on the 2-amino-3-ethoxycarbonyl-amino-6-(p-fluoro-benzylamino)-pyridine gluconate) of gluconic acid.

The gluconic acid can be produced for example by heating an aqueous solution of gluconic acid-Δ-lactone to 60° to 70° C. over at least 30 minutes.

The gluconic acid-Δ-lactone is present in crystalline form so that it is generally more favorable for practical purposes to produce the gluconic acid at times by hydrolysis of the lactone. A more acid pH is caused by addition of acid. Hereby it is recommended not to exceed a pH of 2.0 since otherwise the necessary compatibility for a venous application is impaired.

Solutions of 2-amino-3-ethoxycarbonylamino-6-(p-fluoro-benzylamino)-pyridine gluconate in the stated solvents can also be obtained by mixing the 2-amino-3-ethoxycarbonylamino-6-(p-fluoro-benzylamino)-pyridine together with excess gluconic acid or gluconic acid-Δ-lactone and the solvent in question (polyethylene glycol-water, glycofurol-water, polyethylene glycol-glycofurol-water) (for example by stirring or suspending at a temperature between 20° C. and 80° C. under gasing with nitrogen).

Hereby in case gluconic acid-Δ-lactone is employed in place of gluconic acid, the presence of water is necessary, namely at least 1 mole of water, based on 1 mole of gluconic acid lactone.

The 2-amino-3-ethoxycarbonylamino-6-(p-fluoro-benzylamino)-pyridine gluconate solutions contain e.g. 10 to 50, especially 20 to 40, preferably 35 mg of the free base per ml. For example the content of 2-amino-3-ethoxycarbonylamino-6-(p-fluoro-benzylamino)-pyridine gluconate in an injectable solution is about 55 mg/ml.

The solutions having a 3 fold or 4 fold molar excess of gluconic acid show a pH of 3 to 4 and remain dissolved in clear form even after 7 days storage time at 25° C. and daylight as well as after standing 7 days in the refrigerator at 7° C. without formation of crystals or turbidity. The solutions produced according to the invention accordingly have advantages in stability and in the improved storability.

As solvents there can be used, e.g. polyethylene glycol-water mixtures which contain 10 to 95% or especially 30 to 60, preferably 40% polyethylene glycol (always weight percent), (the polyethylene glycol preferably has an average molecular weight of 200 to 600, especially 300 to 400) or glycofurol-water mixtures which contain 10 to 95%, especially 40% of glycofurol. There can also be employed polyethylene glycol-glycofurol-water mixtures. An especially preferred form contains about 40% polyethylene glycol having an average molecular weight of about 400 and 60% water or 20% glycofurol and 80% water.

The polyethylene glycols employed for example can have the following ranges of molecular weight.

TABLE 1

| Polyethylene Glycol | Molecular Weight Range |
|---|---|
| 200 | 190–210 |
| 300 | 285–315 |
| 400 | 380–420 |
| 600 | 570–630 |
| 1000 | 950–1050 |
| 1540 | 1300–1600 |
| 4000 | 3000–4800 |
| 6000 | 5600–7500 |

Glycofurol (tetrahydrofurfuryl alcohol-polyethylene glycol ether) has a molecular weight of about 190 and has a low toxicity and therefore is suited as medium for injection solutions (R. Budden Arzneimittel-Forschung 28(II), page 1586 (1978). This solution likewise is available commercially.

The injection solutions of the invention besides can contain stabilizers and/or antioxidants such as e.g. sodium disulfite, acetone sodium disulfite, ethylenediamine tetraacetic acid, ascorbic acid and similar materials.

According to a preferred form of the invention the solutions are sterile and are drawn off into sterile containers, for examples into ampoules. Means for sterilizing these solutions are known according to the state of the art. It is preferred to draw off the solutions into ampoules under aseptic conditions as well as under sterile gassing with nitrogen.

Synthesis of
2-Amino-3-ethoxycarbonylamino-6-(p-fluoro-benzylamino)-pyridine Gluconate 3.043 grams (0.01 mole) of 2-amino-3-ethoxycarbonylamino-6-(p-fluoro-benzylamino)-pyridine were suspended in 10 ml of absolute ethanol under gassing with nitrogen and treated in the course of 30 minutes at 60° C. with a solution prepared from 1.781 grams (0.01 mole) of gluconic acid-Δ-lactone in 10 ml of water. The mixture was heated for about 15 minutes at 70° C. until a clear solution formed and then was concentrated to dryness in a vacuum at 60° C. The residue remaining was resteamed with 10 ml of absolute ethanol and dried in a vacuum at 50° C. Yield 4.33 grams (90% of theory) M.P. 117°–123° C. Solubility in water about 0.01%. IR spectrum in KBr: See FIG. 1.

EXAMPLE 1a

"Melt Reaction"

3.043 grams (0.01 mole) of 2-amino-3-ethoxycarbonylamino-6-(p-fluoro-benzylamino)-pyridine were intensively mixed with 1.96 grams (0.01 mole) of gluconic acid and heated under a nitrogen atmosphere for 30 minutes at 140° C. The melt is allowed to cool, triturated with a little 50% ethanol and filtered. It was washed with a little cold ethanol and dried in a vacuum at 50° C. Yield 4.1 grams, M.P. 116°–123° C.

One ampoule contains for example 164.5 mg of 2-amino-3-ethoxycarbonylamino-6-(p-fluoro-benzylamino)-pyridine gluconate.

EXAMPLE 2

The method of manufacture applies for a batch of 20 liters (=6500 ampoules)

Method of Manufacture 1. 10.0 liters of water were heated to 70° C. and after addition of 1562.0 grams of gluconic acid-delta-lactone the solution was allowed to stand for one hour at 70° C. Thereby the solution was gassed with nitrogen.

2. 8000.0 grams of polyethylene glycol molecular weight 380 to 420 were weighed into solution 1 and the solution was heated to 70° C. under gassing with nitrogen.

3. 30.0 grams of sodium disulfite were dissolved in 500.0 ml of water gassed with nitrogen.

4. Solution 3 was added to solution 2.

5. 666.6 grams of 2-amino-3-ethoxycarbonylamino-6-(p-fluoro-benzylamino)-pyridine were sieved through a sieve having a mesh size of 0.3 mm and dissolved in solution 4 under intensive gassing with nitrogen.

6. Solution 5 was cooled off and filled up to 20 liters with nitrogen gassed water.

7. Solution 6 was sterilely filtered through a membrane filter having a pore diameter of 0.2 μm and equipped with a glass fiber first filter.

8. In Process Control:
Measurement of the oxygen content of solution 7 by means of an oxygen electrode. Measurement of the pH-value of solution 7.

9. Solution 7 under aseptic conditions as well as under gassing with nitrogen was filled into colorless ampoules, content 3 ml.

An ampoule contains 164.5 mg of 2-amino-3-ethoxycarbonylamino-6-(p-fluoro-benzylamino)-pyridine gluconate in 3 ml of solution.

The entire disclosure for German priority application P 3416609.2 is hereby incorporated by reference.

What is claimed is:

1. 2-amino-3-ethoxycarbonylamino-6-(p-fluoro-benzylamino)-pyridine gluconate of the formula

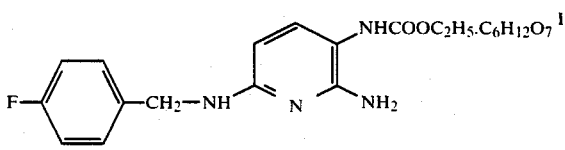

2. A pharmaceutical composition suitable for use as an antiphlogistic agent or an analgetic agent comprising the compound of claim 1 as the active ingredient together with a pharmaceutical carrier or diluent.

3. A pharmaceutical composition for use as an antiphlogistic agent or an analgetic agent comprising the compound of claim 1 in an injectable solution.

4. An injectable solution according to claim 3 wherein the solvent is a mixture of 10 to 95% polyethylene glycol and 5 to about 90% water.

5. An injectable solution according to claim 5 wherein the solvent is a mixture of 10 to 95% glycofurol and 3 to about 80% water.

6. An injectable solution according to claim 3 wherein the solvent is a mixture of 10 to 90% polyethylene glycol, 5 to 85% glycofurol and 5 to about 85% water.

7. An injectable solution according to claim 3 including a pharmaceutically compatible organic acid.

8. An injectable solution according to claim 3 containing an excess of free gluconic acid based on the molar amount of 2-amino-3-ethoxycarbonyl-amino-6-(p-fluoro-benzylamino)-pyridine.

9. An injectable solution according to claim 8 wherein the excess of free gluconic acid is a 3 to 4 fold excess.

10. A solution of the compound of claim 1 in a mixture of 10 to 95% polyethylene glycol and 5 to about 90% water.

11. A solution according to claim 10 containing 10 to 50 mg of the gluconate per ml calculated as the free base.

12. A solution according to claim 11 containing 20 to 40 mg of the gluconate per ml calculated as the free base.

13. A solution of the compound of claim 1 wherein the solvent is a mixture of 10 to 95% glycofurol and 5 to about 80% water.

14. A solution according to claim 13 containing 10 to 50 mg of the gluconate per ml calculated as the free base.

15. A solution according to claim 14 containing 20 to 40 mg of the gluconate per ml calculated as the free base.

16. A solution of the compound of claim 1 wherein the solvent is a mixture of 10 to 90% polyethylene glycol, 5 to 85% glycofural and 5 to about 85% water.

17. A solution according to claim 16 containing 10 to 50 mg of the gluconate per ml calculated as the free base.

18. A solution according to claim 17 containing 20 to 40 mg of the gluconate per ml calculated as the free base.

* * * * *